United States Patent
Arant et al.

(10) Patent No.: US 10,105,190 B1
(45) Date of Patent: Oct. 23, 2018

(54) PLACEMAT SYSTEM (71) Applicant: Neural Analytics, Inc., Los Angeles, CA (US)

(72) Inventors: John Arant, Los Angeles, CA (US); Seth Wilk, Los Angeles, CA (US); Anjan Chatterji, Los Angeles, CA (US)

(73) Assignee: Neural Analytics, Inc., Los Angeles, CA (US)

( * ) Notice: Subject to any disclaimer, the term of this patent is extended or adjusted under 35 U.S.C. 154(b) by 0 days.

(21) Appl. No.: 15/923,906

(22) Filed: Mar. 16, 2018

(51) Int. Cl.
| | |
|---|---|
| *B32B 3/00* | (2006.01) |
| *A61B 46/23* | (2016.01) |
| *B32B 37/14* | (2006.01) |
| *B32B 3/06* | (2006.01) |
| *B32B 3/08* | (2006.01) |
| *B32B 7/12* | (2006.01) |
| *B32B 37/20* | (2006.01) |
| *B32B 37/12* | (2006.01) |
| *A61B 8/00* | (2006.01) |
| *A61B 50/36* | (2016.01) |
| *B32B 7/02* | (2006.01) |
| *A61B 50/30* | (2016.01) |
| *A61B 46/20* | (2016.01) |
| *A61B 50/00* | (2016.01) |

(52) U.S. Cl.
CPC ............... *A61B 46/23* (2016.02); *A61B 8/40* (2013.01); *A61B 50/36* (2016.02); *B32B 3/06* (2013.01); *B32B 3/08* (2013.01); *B32B 7/02* (2013.01); *B32B 7/12* (2013.01); *B32B 37/1207* (2013.01); *B32B 37/144* (2013.01); *B32B 37/20* (2013.01); *A61B 2046/205* (2016.02); *A61B 2050/0071* (2016.02); *A61B 2050/3011* (2016.02); *A61B 2050/314* (2016.02); *B32B 2037/1215* (2013.01); *B32B 2307/7145* (2013.01); *B32B 2307/726* (2013.01); *B32B 2307/7265* (2013.01); *B32B 2535/00* (2013.01)

(58) Field of Classification Search
CPC ....... B32B 3/06; B32B 3/08012; A61B 46/00; A61B 50/36
See application file for complete search history.

(56) References Cited

U.S. PATENT DOCUMENTS

| | | | | |
|---|---|---|---|---|
| 3,576,039 | A * | 4/1971 | Roberts | A61F 5/485 5/484 |
| 5,082,707 | A * | 1/1992 | Fazio | A47G 9/062 428/43 |
| 6,341,393 | B1 * | 1/2002 | Votel | A61G 7/1015 5/484 |
| 7,120,952 | B1 * | 10/2006 | Bass | A47C 27/006 5/484 |
| 8,042,688 | B2 | 10/2011 | Parks et al. | |

* cited by examiner

*Primary Examiner* — Elizabeth E Mulvaney
(74) *Attorney, Agent, or Firm* — Foley & Lardner LLP (57) ABSTRACT

A disposable placemat system is provided. The disposable placemat system includes a sheet of a first material having a front surface and a back surface opposite to the front surface. The disposable placemat system includes a sheet of a second material attached to the sheet of the first material at the front surface. The first material is liquid impermeable and different from the second material. The second material is absorbent and configured to absorb a fluid used in conjunction with a medical procedure utilizing acoustic energy to monitor a subject.

20 Claims, 10 Drawing Sheets

PLACEMAT SYSTEM

BACKGROUND

For providing more effective healthcare, maintaining hygiene and cleanliness is a high priority for healthcare providers. One scenario in which hygiene may be compromised is when medical materials and instruments (e.g., placemats and sheets) are reused on different patients, which may enable and/or accelerate the transfer of bacteria or illness from patient to patient. In addition, reusable medical instruments and materials may be cumbersome for use by a healthcare provider, for example, due to storing, deploying, safekeeping, monitoring, and the like, of the reusable equipment.

SUMMARY

According to various arrangements, provided is a placemat system that is disposable such that it is not reused between more than one subject. In addition, according to various arrangements, the placemat system is straightforward to use. As such, hygiene and cleanliness are increased, while allowing healthcare providers to more efficiently and easily use the system.

According to various arrangements, there is provided a disposable placemat system for containing medical materials and instruments. The disposable placemat system includes a sheet of a first material having a front surface and a back surface opposite to the front surface. The disposable placemat system includes a sheet of a second material attached to the sheet of the first material at the front surface. The first material is liquid impermeable and different from the second material. The second material is made from an absorbent material configured to absorb a fluid used in conjunction with a medical procedure utilizing acoustic energy to monitor a subject.

In some arrangements, the sheet of the second material has a thickness greater than that of the sheet of the first material.

In some arrangements, the sheet of the second material is permanently attached to the sheet of the first material.

In some arrangements, the sheet of the second material is hot-melt glued to the sheet of the first material.

In some arrangements, the disposable placemat system further includes one or more anchors attached to the sheet of the first material.

In some arrangements, the one or more anchors includes a plurality of anchors, each of the plurality of anchors attached at a respective corner of the placemat system at the sheet of the first material.

In some arrangements, the plurality of anchors includes four anchors.

In some arrangements, the one or more anchors are attached to the front surface of the sheet of the first material.

In some arrangements, the one or more anchors include an adhesive layer and are configured to retain one or more medical instruments to be used during the medical procedure via the adhesive layer.

In some arrangements, the one or more anchors are attached to the back surface of the sheet of the first material.

In some arrangements, the one or more anchors include an adhesive layer and are configured to removably attach the placemat system to a work surface on which the placemat system is placed via the adhesive layer.

In some arrangements, the one or more anchors include a weighted block for retaining the placemat system at a work surface on which the placemat system is placed.

In some arrangements, the placemat system defines a drawstring casing around a perimeter of the placemat system, and wherein the placemat system includes a drawstring through the drawstring casing that extends outside of the placemat system from the drawstring casing.

In some arrangements, the placemat system further includes a length of elastic string extending from the placemat system and configured to be tied around a bed or gurney for stabilizing the placemat system to the bed or gurney.

In some arrangements, the placemat system further includes a plurality of placemat systems and a roll configured to store the plurality of placemat systems.

In some arrangements, each adjacent pair of placemat systems of the plurality of placemat systems is separated by a perforated section such that the adjacent pair of placemat systems is configured to be detached from each other via the perforated section.

In some arrangements, the fluid includes ultrasound gel.

In some arrangements, the sheet of the second material includes an anti-bacterial compound.

In some arrangements, the placemat system further includes a layer of a chemical compound at the back surface of the sheet of the first material, the chemical compound being anti-bacterial and configured to sterilize ultrasound equipment.

In some arrangements, a method of manufacturing a disposable placemat system includes providing a sheet of a first material having a front surface and a back surface opposite to the front surface; and providing a sheet of a second material attached to the sheet of the first material at the front surface, the first material being liquid impermeable and different from the second material and the second material being absorbent and configured to absorb a fluid used in conjunction with a medical procedure utilizing acoustic energy to monitor a subject.

BRIEF DESCRIPTION OF THE FIGURES

Features, aspects, and advantages of the present invention will become apparent from the following description and the accompanying example arrangements shown in the drawings, which are briefly described below.

DETAILED DESCRIPTION

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details. In some instances, well-known structures and components are shown in block diagram form in order to avoid obscuring such concepts.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure.

Figure 1:
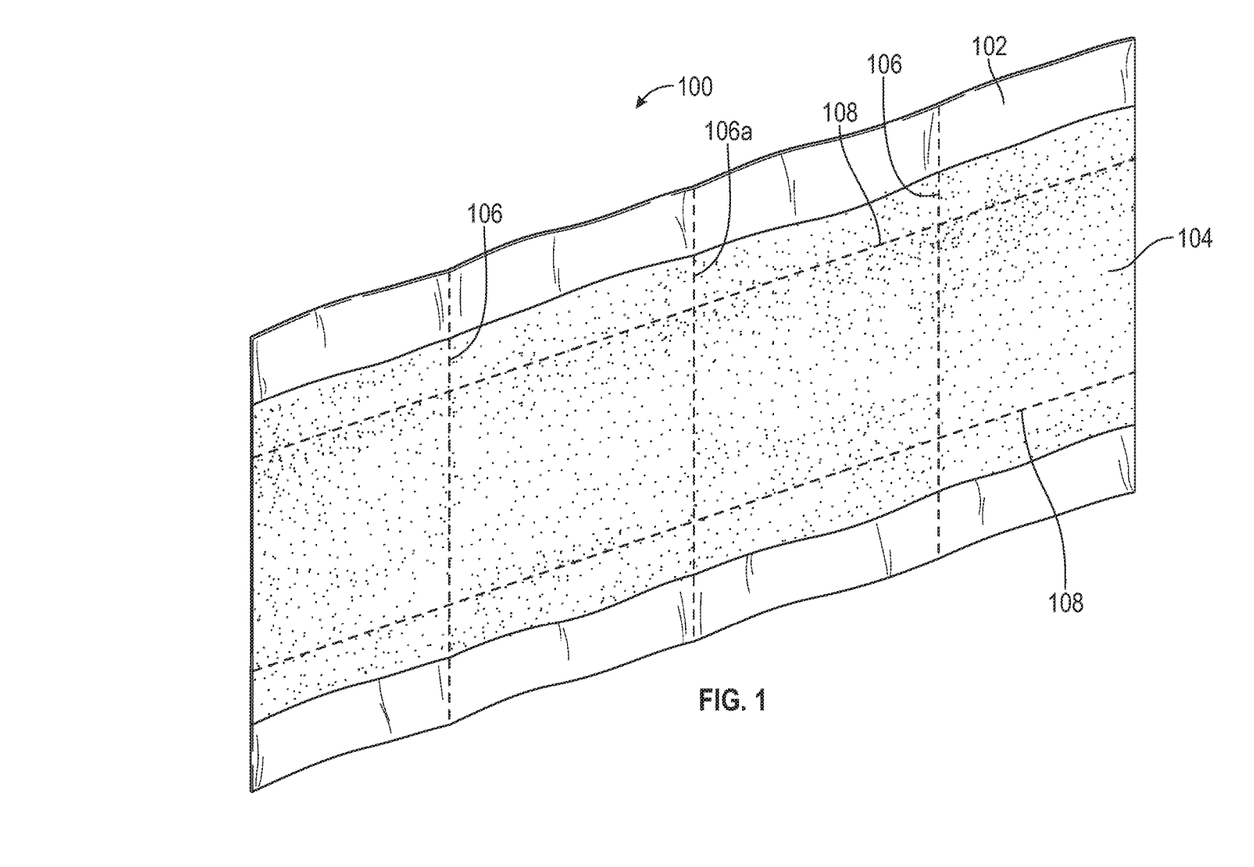
FIG. 1 illustrates a top view of a placemat system according to various arrangements.

FIG. 1 illustrates a top view of a placemat system 100 according to various arrangements.

Referring to FIG. 1, in some arrangements, the placemat system 100 is made from a sheet of a first material 102 and a sheet of a second material 104. The first material 102 includes any suitable flexible material, such as, but not limited to, fabric, plastic, and the like. In some arrangements, the first material 102 is a stretchable or elastic material. In some arrangements, the first material includes a slick material or is coated with a slick material to allow frictionless movement along a surface. For example, the first material 102 can be made from or coated with a water-repellent material, hydrophobic material, or a superhydrophobic (nanoscopic surface) material. In some examples, the first material 102 is slippery to allow the frictionless movement of an object (e.g., a head of a subject, a medical instrument, and the like) on the surface of the first material 102. Examples of the first material 102 include, but are not limited to, polytetrafluoroethylene (PTFE), waterproof composite fabric, and the like. In some arrangements, the second material 104 is made from any suitable soft, absorbent material, such as, but not limited to, paper, cotton, rayon, polyester, polyethylene, polypropylene, fiber, sponge, polyethylene terephthalate, wood pulp, combinations thereof, and the like. In particular arrangements, the second material 104 is made from a soft material that is configured to cushion a subject when placed thereon for added comfortability of the subject. In that regard, the sheet of the second material 104 may have a suitable thickness for providing the cushion. In some arrangements, both the first material 102 and the second material 104 are made from a relatively inexpensive material such that the placemat system 100 can be mass-produced and disposed of after a single use.

In some arrangements, the second material 104 is configured to be absorbent with respect to one or more fluids so as to aid in healthcare administration by, for example, cleaning a patient or equipment before, during, or after a medical procedure. In some arrangements, fluids that are used in a medical procedure can be absorbed by the sheet of the second material 104. Examples of the fluids include, but are not limited to, an ultrasound gel, disinfectants (rubbing alcohol or another liquid disinfectant), water, and the like. In some arrangements, bodily fluids from a patient can be absorbed by the sheet of the second material 104. Examples of the bodily fluids include, but are not limited to, blood, urine, vomit, fecal matter, pus, saliva, and the like. For example, the sheet of second material 104 can have a large enough area to encompass a body of an infant or toddler that can be placed on the sheet of second material 104 for medical examination or procedure, and any fluids discharged from the infant or toddler or used in connection with the medical examination or procedure can be absorbed by the sheet of the second material 104.

In some arrangements, using the placement system 100 in the manner disclosed allow a work surface for the medical examination or procedure on which the placemat system 100 is positioned to remain clean and sterile from subject to subject, resulting in increased infection control and higher quality medical care. For example, in the case where a patient has experienced mild traumatic brain injury and is to undergo a brain diagnostic (e.g., Transcranial Doppler) to confirm, the patient may be bleeding from the experience and the placemat system 100 can be used to form a barrier between the patient and a surface (e.g., a surface of a table, a bed, the ground, and the like) on which medical procedures occur such that the surface can remain sterile from such bodily fluids. In addition, the sheet of second material 104 can be utilized to help absorb and clean the blood from the patient.

In some arrangements, the sheet of the second material 104 is configured to retain or absorb fluids that are involved in different medical procedures. For example, in some situations in which the subject is bleeding, the sheet of the second material 104 is configured to have sufficient absorbency, thickness, and size to be capable of wiping and retaining the blood from the subject so that the medical procedure can be properly performed. In such arrangements, the sheet of the second material 104 is made from materials capable of absorbing or retaining blood, such as, but not limited to, cotton, rayon, polyester, polyethylene, polypropylene, combinations thereof, and the like.

As another example, in some situations in which fluids (e.g., such as but not limited to, ultrasound gel for facilitating ultrasound signal propagation from an ultrasound probe into a subject's body) are used in conjunction with a medical procedure, the sheet of the second material 104 is configured to have sufficient absorbency, thickness, and size to be capable of wiping, retaining, and/or absorbing the ultrasound gel from the subject during or after the medical procedure. Accordingly, in some arrangements, the sheet of the second material 104 aids in the administration of healthcare by allowing a user to clean the patient of any medical fluids (e.g., ultrasound gel) with edges or corners of the sheet of the second material 104 or physically guide the fluid applied to the patient or a piece of medical equipment to optimal locations, by a user via the sheet of the second material 104, for increasing the effectiveness of the medical procedure (e.g., the ultrasound gel can be physically directed and constrained, via use of the sheet of the second material 104, to an acoustic window at a subject's head that is optimal for receiving the ultrasound signal). Accordingly, in some arrangements, the sheet of the second material 104 is made from materials capable of absorbing or retaining ultrasound gel, such as, but not limited to, wood pulp, resin, paper sheets, cotton, polyester, rayon, polyethylene, polypropylene, combinations thereof, and the like.

In some arrangements, one or more of the first material 102 and the second material 104 can be made from or include a pliable material, such as, but not limited to, a shape memory polymer or metal material. In some examples, a sheet of the first material 102 and/or a sheet of the second material 104 include a layer of pliable material embedded therein to allow bending of the sheet of the first material 102 and/or the sheet of the second material 104. In practice, a user can, for example, bend edges or corners of the sheet of the first material 102 and/or the sheet of the second material 104 to form raised edges and/or corners. The raised edges and/or corners can prevent the fluids from flowing to the surface upon which the placemat system 100 is positioned. The pliable material may be within the sheet of the first material 102 and/or the sheet of the second material 104 or on either surface of the sheet of the first material 102 and/or the sheet of the second material 104. In some arrangements, the sheet of the first material 102 and the sheet of the second material 104 are made from any suitable pliable material so that the placemat system 100 can be positioned on any irregular surface such that the placemat system 100 will conform to the surface. The pliable material allows a user to fold edges of the first material 102 up to form a basin or partial basin, trapping all or some of the medical fluids or bodily fluids within an interior volume defined by the basin or partial basin. In some arrangements, the pliable material includes, but is not limited to, plastic (e.g., including a plurality of joints for forming the shape), leather, nylon, and the like.

In some arrangements, the sheet of second material 104 is made from a permeable fabric, and the sheet of first material 102 is made from a fluid impermeable fabric. A resilient absorbent material is secured between the first and second sheets, for example, by stitching or quilting the sheets and cushioning the materials 102 and 104 together using sterile joining practices for medical mats. The number and combination of sheets can be varied to accommodate absorption, sterility, volume, density, thickness, and other material properties. When the placemat system 100 is used to define a carrying bag (as further discussed below), the sheet of second material 104 forms an interior surface of the carrying bag, and the sheet of first material 102 forms an exterior surface of the carrying bag. In some arrangements, the layer of absorbent material and/or the second material 104 includes a sterile fluid retention-capable medical fiber.

In some arrangements, the sheet of the first material 102 is fluid-impermeable so that fluids that are absorbed by the sheet of the second material 104 do not pass beyond the sheet of first material 102, providing increased infection control because the fluids are contained within the placemat system 100 that can be disposed of. For example, the surface upon which the placemat system 100 is positioned can remain sterile and clean due to the fluid impermeable first material 102. Any other objects are also protected as the placemat system 100 is disposed of since the first material 102 will not allow leakage of fluid outside of the placemat system 100 (e.g., when the placemat system 100 is cinched or folded up for disposal). In other arrangements, the second material 104 is made from any suitable fluid impermeable material, such as, but not limited to, glass, plastic, metal, polytetrafluorothylene (PTFE), coated fabrics, silicone, polyurethane, rubber, rubber-coated textiles, combinations thereof, and the like. Furthermore, the sheet of the first material 102 and the sheet of the second material 104 have any suitable thickness to be sufficiently thin for storage (e.g., when folded up).

In some arrangements, the first material 102 has a larger surface area than that of the second material 104. In some arrangements, the second material 104 has a thickness greater than that of the first material 102. The first material 102 is affixed to the second material 104 by any suitable and secure method, such as, but not limited to, by adhesive (e.g., hot-melt glue), by thermo-forming, by sewing, by molding, by welding, by Velcro, by stapling, and the like. In some arrangements, the second material 104 extends along an entire length of the first material 102, but not along an entire width of the first material 102, or vice versa. The length of the first material 102 is greater than the width of the first material 102. In other arrangements, the second material 104 extends along the entire width and the entire length of the first material 102. In other arrangements, all sides of the sheet of the second material 104 are encompassed by the sheet of the first material 102 (e.g., the sheet of the second material 104 has a square shape within the larger rectangular sheet of the first material 102). In some arrangements, the placemat system 100 is designed to have a rectangular shape. In other arrangements, the placemat system 100 is designed to have any suitable shape (such as, but not limited to, a circle, a triangle, a hexagon, and the like) for receiving a patient or a specific body part of the patient.

In some arrangements, the placemat system 100 includes one or more free pieces of string or another component protruding/extending from one or more corners of the placemat system 100. In some arrangements, the strings are affixed to the placemat system 100 by any suitable and secure method, such as, but not limited to, by adhesive (e.g., hot-melt glue), by thermo-forming, by sewing, by molding, by welding, by Velcro, by stapling, and the like. In some arrangements, the strings can be used to tie up the placemat system 100 after use thereof. For example, the placemat system 100 can be folded up or otherwise closed upwards (e.g., around the sheet of the second material 104) and then tied up with the strings such that the placemat system 100 remains closed and capable of easy disposal.

In some arrangements, the placemat system 100 has any suitable size for receiving a body part or the entire body of a patient. For example, in arrangements where the placemat system 100 is configured to receive a head of a patient, the sheet of the first material 102 can have a length in a range of about 30 centimeters (cm) to about 95 cm and a width in a range of about 25 cm to about 65 cm. In such arrangements, the sheet of the second material 104 can have a length in a range of about 30 cm to about 95 cm and a width in a range of about 20 cm to about 50 cm. In such arrangements, the sheet of the second material 104 has a size and position at the sheet of the first material 102 such that a first strip of the first material 102 is located above the sheet of the second material 104 and a second strip of the second material 104 is located below the sheet of the first material 102 (e.g., the non-limiting configuration shown in FIG. 1). In some arrangements, the first strip and the second strip of the first material 102 has the same width, which is in a range from about 4 cm to about 9 cm. In some arrangements, the sheet of the second material 104 has any suitable weight for absorbing and cushioning a patient, such as, but not limited to, in a range from about 50 grams per square meter (gsm) to about 110 gsm. In some arrangements, the sheet of the second material 104 has any suitable absorbency characteristic for absorbing fluids thereon, such as absorbency in a range of about 4 grams of fluid to about 30 grams of fluid (e.g., blood or ultrasound gel). The absorbency can be a measurement of how much fluid the second material 104 holds before leaking therefrom, as determined by, for example, the Syngina Test.

In some arrangements, the placemat system 100 is foldable (e.g., for simple and easy storage and disposal thereof). In some arrangements, the placemat system 100 includes at least one vertical folding guide 106 and at least one horizontal folding guide 108. In some arrangements, the folding guides 106, 108 provide sections along which the placemat system 100 can be folded such that the placemat system 100 can be folded into a smaller form factor to allow convenient, easy storage and transportation of the placemat system 100. For example, the placemat system 100 includes a plurality of vertical folding guides 106 and/or a plurality of horizontal folding guides 108. The placemat system 100 includes any desired number and orientation of vertical folding guides 106 and horizontal folding guides 108 to facilitate suitable miniaturization of the placemat system 100.

In some arrangements, the second material 104 or an additional material between the first material 102 and the second material 104 is or includes a cushioning material for providing a comfortable experience to a patient. In particular arrangements, the cushioning material is concentrated in a substantially central portion of the placemat system 100. For example, the cushioning material can be located between the two vertical folding guides 106 directly surrounding a center vertical line of the placemat system 100 (e.g., the center vertical line in an example may fall along the central vertical folding guide 106a). In other arrangements, the cushioning material is located over an entirety of the second material 104.

Accordingly, in some arrangements, the placemat system 100 can be used with respect to a patient, for example, by being placed underneath the patient (e.g., underneath the patient's head) while the patient is being treated. For example, the patient may be scanned by a Transcranial Doppler (TCD) system for which ultrasound gel needs to be applied to the patient's head or to the system, and the ultrasound gel can be easily wiped off by the second material 104. As another example, the patient may have experienced head trauma, and thus the second material 104 can be used to clean the patient's head (e.g., of dirt, debris, blood, and the like) to be in a suitable state for use with respect to a medical device (e.g., a TCD). Furthermore, in some arrangements, the placemat system 100 serves as a physical barrier between the patient and any repeatedly-used surface (e.g., a gurney, hospital bed, and so on), thereby providing increased infection and hygiene control between patients.

In some arrangements, the sheet of the second material 104 is pre-soaked or treated with a compound configured to be a disinfectant or to kill bacteria. In particular arrangements, the second material 104 is pre-soaked or treated with, for example, but not limited to, alcohol, ethanol, isopropanol, dodecanoic acid, triclosan, triclocarban, a combination thereof, and the like. In some arrangements, the compound at the second material 104 is safe to contact skin of the subject. In some arrangements, an extra layer of a disposable thin film is applied to the patient-facing surface of the sheet of the second material 104 such that the film prolongs the lifespan of the treated second material 104 such that the compound therein does not dry out during storage. In other arrangements, the back surface of the sheet of the first material 102 (e.g., the surface that is opposite to the surface connected to the sheet of the second material 104) is treated with the compound such that when the placemat system 100 is positioned on a work surface, the work surface is disinfected for increased sterility and hygiene. When the placemat system 100 is positioned on the work surface, the back surface comes in contact with the work surface. For example, another sheet of the second material 104 can be affixed to the back surface of the sheet of the first material 102 and pre-soaked or treated with a disinfecting or antibacterial compound. Accordingly, by including a layer of disinfecting or antibacterial compound on the back surface of the sheet of the first material 102, the placemat system 100 also serves as a sterilization apparatus that sterilizes the work surface on which the placemat system 100 is positioned (e.g., a medical examination bed, gurney, table, and so on). Furthermore, by including a layer of disinfecting or antibacterial compound on the back surface of the sheet of the first material 102, the chemical compound does not contact the skin of the subject, which may otherwise cause irritation to the subject (e.g., for those chemical compounds that are not recommended or safe to contact subject's skin). In other arrangements, the disinfecting or antibacterial compound is included at both the front and back surfaces of the placemat system 100.

In some arrangements, the front surface and/or the back surface of the sheet of the first material 102 includes a disinfecting wipe that is configured to disinfect ultrasound equipment without damaging such equipment. In some arrangements, the disinfecting solution of the disinfecting wipe is soaked or treated within the sheet of the second material 104 (e.g., at one or more of the back or front surfaces of the sheet of the first material 102). In other arrangements, at least one standalone ultrasound equipment disinfecting wipe is included in the placemat system 100, such as at a corner, in a packaging stored therein, and so on. A problem with using other wipes that are not designed for use with ultrasound equipment is that the non-ultrasound equipment wipes may damage the equipment. For example, alcohol and solvents can dry and crack cables, touchscreens can become unresponsive to touch, and ultrasound probes can be damaged so as to compromise their imaging effectiveness. Thus, according to some arrangements, the disinfecting wipes or disinfecting solution soaked or treated within the placemat system 100 can be compatible with ultrasound equipment and can be made from such compounds as, but not limited to, water, decyldimethyloctylammonium chloride, dimethyldioctylammonium chloride, didecyldimethylammonium chloride, quaternary ammonium compounds, benzyl-C12-16-alkyldimethyl, combinations thereof, and the like. As such, the chemical compound as described above can have antibacterial, disinfecting, and ultrasound equipment compatibility characteristics. The disinfecting wipes can include a membrane, a cover, or a container for retaining the disinfecting solution.

In some arrangements, a disinfecting wipe or at least a portion of thereof is positioned on the patient-facing surface of the second material 104, such that overflowing disinfecting solution of the disinfecting wipe can be absorbed by the second material 104. In that regard, the disinfecting wipe is positioned sufficiently far away from a center of a plane defined by the second material 104 so that the bodily fluids and other medical solutions do not contaminate or mix with the disinfecting solution of the disinfecting wipe. In some arrangements, a disinfecting wipe or at least a portion of thereof is positioned on a portion of the patient-facing surface of the first material 102 that is not covered by the second material 104. For example, one or more disinfecting wipe or at least a portion thereof is positioned on the top and bottom strips or the corners of the first material 102 that is not covered by the second material 104. When a head of the patient is placed on a center of the placemat system 100, the placemat system 100 (including the sheets of the first and second materials 102 and 104) may become concave due to the weight of the head. This may cause the edges (e.g., the top and bottom strips) of the first material 102 to become raised as compared to the center of the placemat system 100. As such, overflowing disinfecting solution of the disinfecting wipe can flow toward the center of the placemat system 100 from the first material 102 and become absorbed by the second material 104 when the overflowing disinfecting solution of the disinfecting wipe comes in contact with the second material 104.

Figure 2:
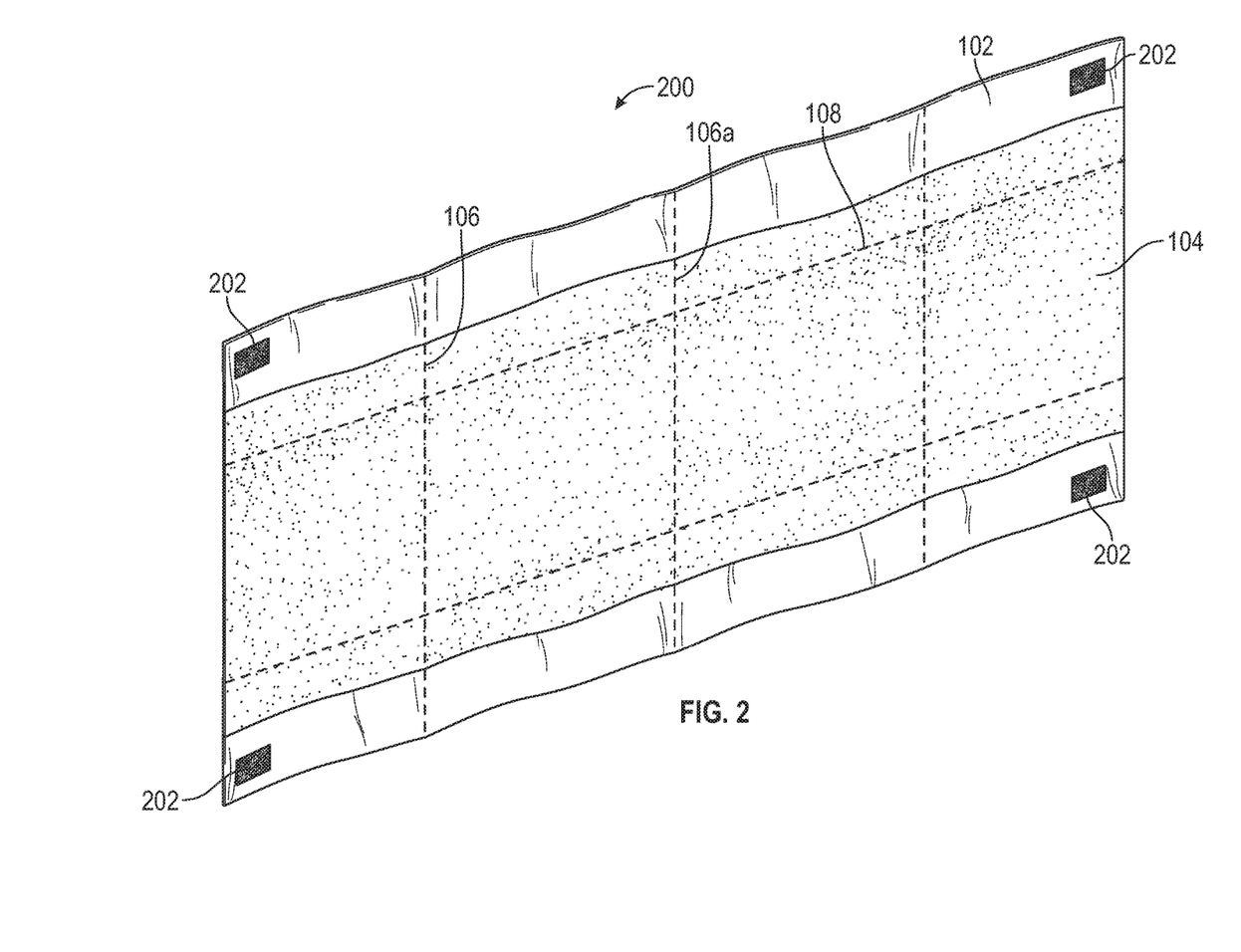
FIG. 2 illustrates a top view of a placemat system including one or more anchors according to various arrangements.

FIG. 2 illustrates a top view of a placemat system 200 including one or more anchors 202 according to various arrangements.

Referring to FIG. 2, the placemat system 200 may include at least the placemat system 100, for example, having a sheet of the first material 102, a sheet of the second material 104, folding guides 106, 106a, and 108, and the like. In some arrangements, the anchors 202 are located at one or more corners of the placemat system 200. In some arrangements, one of the anchors 202 is located at each of the corners of the placemat system 200. In some arrangements, the anchors 202 are configured to restrain the placemat system 200 to the work surface upon which the placemat system 200 rests. For example, the anchors 202 can include weights (e.g., a weighted block of material such as metal or metal alloy) that are configured to secure the placemat system 200 to the work surface to provide a more stable area for placing a patient. In other arrangements, the anchors 202 include an adhesive or adhesive layer located at a back surface (opposite to the patient-facing front surface) of the first material 102 such that the placemat system 200 can be affixed to the work surface via the adhesive anchors 202. In particular arrangements, each of the anchors includes an adhesive layer on an outer surface of the anchor 202 for contacting a work surface on which the placemat system 200 is placed such that the placemat system 200 is removably attached to the surface. In some arrangements, the anchors 202 are located at predetermined intervals along the edge of the placemat system 200, for example, along the top and bottom strips of the sheet of the first material 102 that do not have any of the second material 104 attached thereto.

In some arrangements, the anchors 202 are located at the front surface of the placemat system 200. In such arrangements, the anchors 202 are configured to receive and hold instruments, materials, tools, or other objects that are used in a medical procedure for easy storage and access by a healthcare provider. In particular arrangements, each of the anchors 202 include an adhesive layer on its outer surface (the patient-facing surface), as described above. For example, the anchors 202 can be configured to retain a gel applicator, pincers, a scalpel, gauze, alcohol wipes, and any other medical-related object to be used in connection with a medical procedure. In such arrangements, the anchors 202 (e.g., front surface anchors) include any suitable material for retaining one or more objects, such as, but not limited to, magnets, adhesive (e.g., double-sided tape), Velcro, sticky gel, hooks, rings, and the like. In some arrangements, the anchors 202 are located at both the front surface and the back surface of the placemat system (e.g., the sheet of the first material 102) for added stability. As such, the anchors 202 may perform dual functions of stabilizing the placemat system 200 (with the additional weight of the objects) and holding the objects in place during a medical procedure. In some arrangements, each of the anchors 202 includes a guard made of rigid or semi-rigid material (e.g., disinfected plastic, cardboard, and the like) raised from and traverses the plane defined by the placemat system 200. The guard is between the center of the placemat system 200 and the rest of one of the anchors 202 to prevent the objects retained by one of the anchors 202 from sliding toward the patient when the patient is placed in the center of the placemat system 200.

In some arrangements, the anchors 202 include one or more strings or bands that are configured to be tied to a work surface on which the placemat system 200 is positioned (e.g., a bed, gurney, hospital table, and the like). In some arrangements, the strings or bands are elastic loops that are configured to wrap around the work surface. In particular arrangements, one or more lengths of string extend from the placemat system 200 and are configured to be tied to each other and around the work surface. In some arrangements, a first length of string extends from one side of the placemat system 200 and a second length of string extends from a second side of the placemat system 200. The first and second lengths are configured to be tied together and around the work surface on which the placemat system 200 is placed. In some arrangements, more than one pair of strings is included such that each corresponding pair is tied together. In other arrangements, the length of string is an elastic loop (e.g., rubber band) such that it can be expanded such that the work surface can be inserted through the elastic loop such that the elastic loop contracts or snaps against the work surface, thereby stabilizing the placemat system 200 with respect to the work surface. In some arrangements, the elastic loop is positioned at a back surface of the placemat system 200.

In some arrangements, the back surface (opposite of the patient-facing surface) of the placemat system 200 is coated with an adhesive compound such that the placemat system 200 is configured to be affixed to the work surface on which the placemat system 200 is positioned. In some arrangements, the first material 102 is made from a material that tends to cling to a surface (e.g., through friction, electrostatic charge, and so on), such as, but not limited to, Polyvinylidene Chloride (PVC), Low-Density Polyethylene (LDPE), cellophane, and the like. In some arrangements, the anchors 202, strings, bands, adhesive, and the like provide stability of the placemat while underneath the patient such that movement of the patient does not disturb the positioning of the placemat system 200, for example, so that the placemat system 200 falls on the ground, shifts underneath the patient, and so on.

Figure 3A:
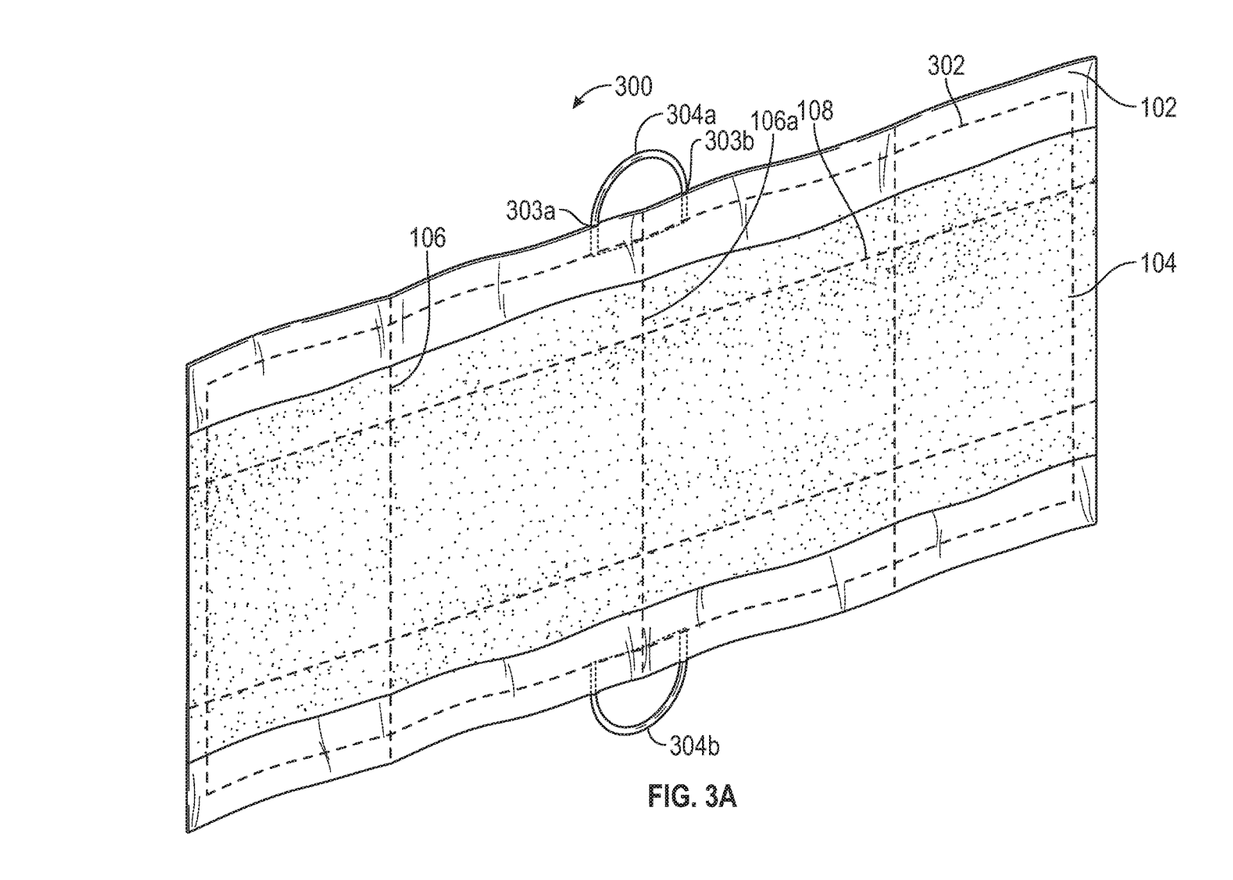
FIG. 3A illustrates a top view of a placemat system including one or more drawstrings according to various arrangements.

FIG. 3A illustrates a top view of a placemat system 300 including one or more drawstrings 304a, 304b according to various arrangements.

Referring to FIG. 3A, the placemat system 300 may include at least the placemat system 100, for example, having a sheet of the first material 102, a sheet of the second material 104, the folding guides 106, 106a, and 108, and the like. In some arrangements, the placemat system 300 includes a hem that extends about the entire periphery of the placemat system 300 to define a drawstring casing 302 or passageway. In some arrangements, the drawstring casing 302 is formed by sewing or welding the edges of the drawstring casing together 302 to provide a tunnel therebetween that defines the drawstring casing 302. For example, at portions where the first material 102 and the second material 104 overlap, the edges of the drawstring casing 302 can be sewn or welded shut such that the drawstring casing 302 is interposed between the sheet of the first material 102 and the sheet of the second material 104.

In some arrangements, the placemat system 300 includes a top drawstring 304a and a bottom drawstring 304b. In some arrangements, the drawing strings 304a and 304b are different portions of a same drawstring. In other arrangements; the drawing strings 304a and 304b are different drawstrings. Each drawstring 304a, 304b extends from the placemat system 300 from the drawstring casing 302. The top drawstring 304a and the bottom drawstring 304b are located at substantially central locations along the length of the placemat system 300 such that the placemat system 300 can be adequately miniaturized and transformed into a carrying bag form by a user that pulls on the drawstrings 304a, 304b.

In some arrangements, the top drawstring 304a is designed as a loop shape such that a user can easily grab onto and pull the top drawstring 304a away from the placemat system 300. In some arrangements, the top drawstring 304a straddles a top midpoint of the placemat system 300 that is defined by the central vertical folding guide 106a. For example, the upper edge or portion near the upper edge of the placemat system 300 defines two openings 303a and 303b that straddle the upper midpoint of the placemat system 300, and the top drawstring 304a enters the placemat system 300 through the openings 303a and 303b such that the top drawstring 304a is in communication with the drawstring casing 302.

In other arrangements, the top drawstring 304a and the corresponding openings 303a, 303b are located at a different location other than proximate the upper midpoint of the placemat system 300, such as, but not limited to, a side midpoint (e.g., 90 degrees from the upper midpoint), a location that is not a midpoint, a corner, and the like. In other arrangements, the top drawstring 304a is not a loop, but any other suitable shape or design for allowing a user to pull therefrom, such as, but not limited to, knotted individual strands (e.g., each strand extending from respective openings 303a and 303b) and the like. In other arrangements, the placemat system 300 defines one opening 303a (e.g., at the upper midpoint) from which the drawstring 304a extends. In some arrangements, the placemat system 300 includes any suitable number of drawstrings for miniaturizing itself, such as, but not limited to, one, three, four (e.g., at each horizontal and vertical edge midpoints), and so on. In some arrangements, the top drawstring 304a is made from any suitable material, such as, but not limited to, nylon, cloth, plastic, and the like. In some arrangements, the bottom drawstring 304b includes similar or the same features as those described above with respect to the top drawstring 304a.

As such, in some arrangements, by providing the top drawstring 304a and the bottom drawstring 304b, the placemat system 300 can be cinched up and disposed of. For example, any other disposable materials part of a medical procedure can be placed within the placemat system 300 and then the placemat system 300 can be cinched up for disposal of the placemat system 300 and the materials inserted therein. Accordingly, the placemat system 300 allows for efficient deployment and efficient disposal thereof by a healthcare administrator.

In other arrangements, instead of drawstrings 304a, 304b, the placemat system 300 (and any disposable materials placed therein) can be folded up and disposed of. For example, the side edges can include handles attached thereto such that a user can fold the placemat system 300 and carry it away for disposal.

Figure 3B:
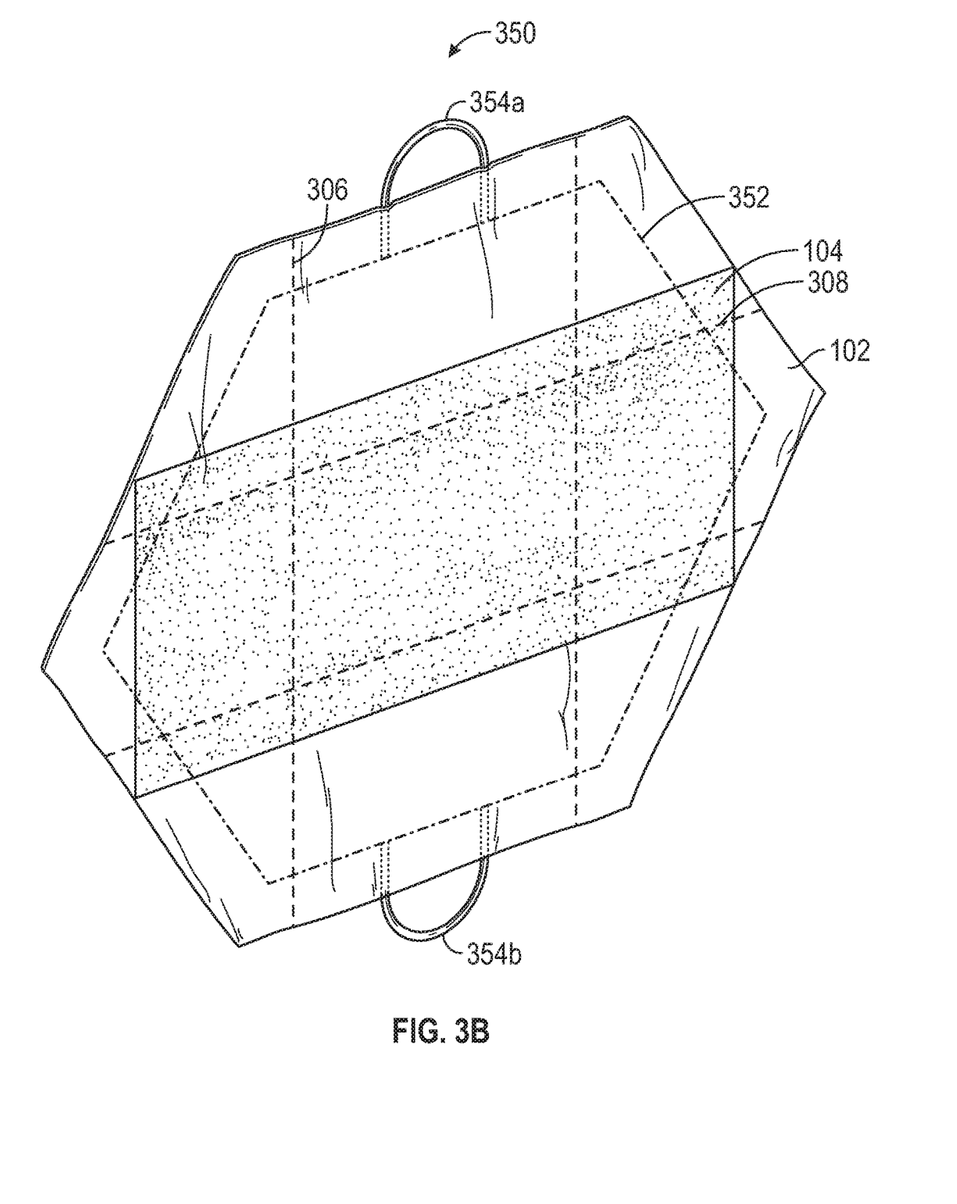
FIG. 3B illustrates a top view of a placemat system including one or more drawstrings according to various arrangements.

FIG. 3B illustrates a top view of a placemat system 350 including one or more drawstrings 354a, 354b according to various arrangements. Referring to FIGS. 3A-3B, the placemat system 350 is similar to the placemat system 300 in that the placemat system 350 includes the first material 102, the second material 104, and folding guides 306 and 308.

In some arrangements, the placemat system 350 is in a hexagonal shape. In other arrangements, the placemat system 350 is any suitable shape for being placed underneath a subject and/or for enabling transformation into a carrying bag, such as, but not limited to, a triangle, a square, a pentagon, and so on. The hexagonal shape may allow the placemat system 350 to readily form a bag.

Figure 3C:
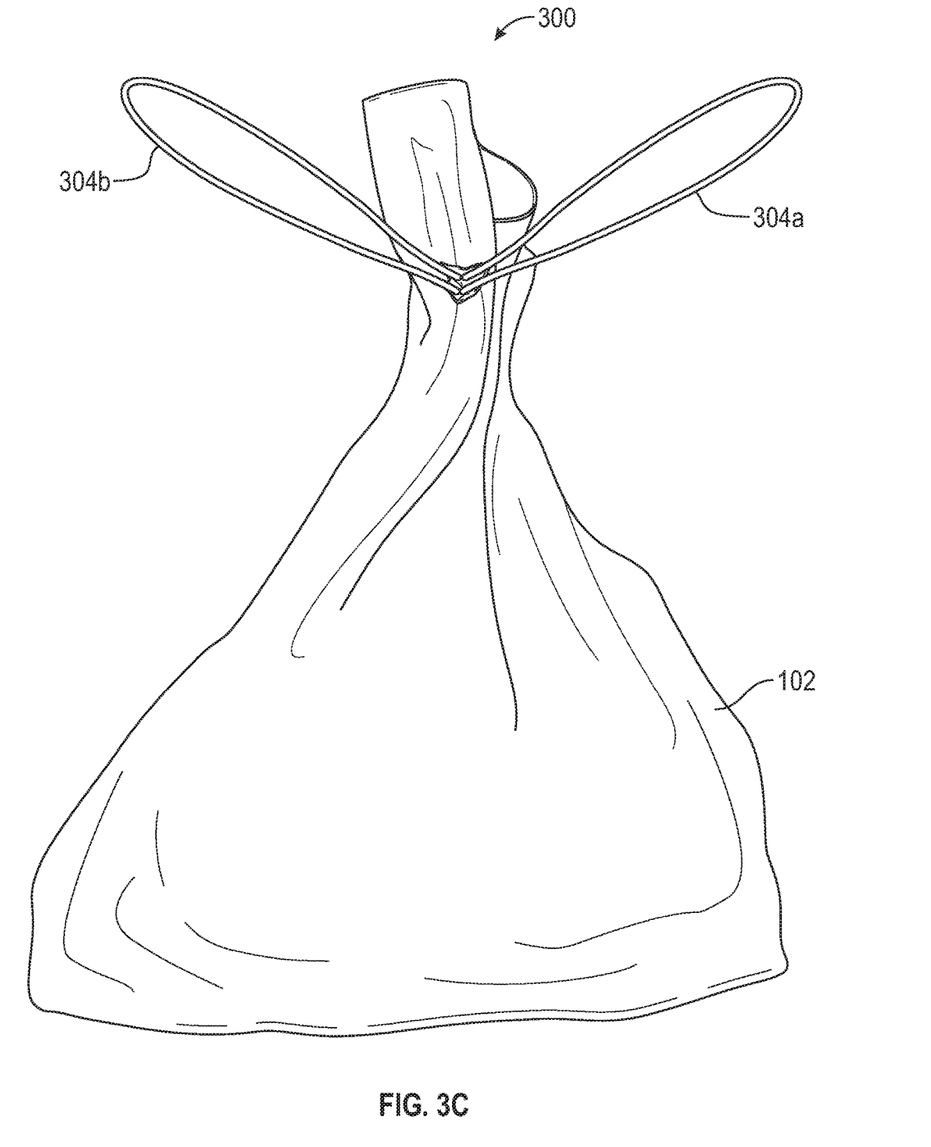
FIG. 3C illustrates a perspective view of the placemat system shown in FIG. 3A that is transformed into a carrying bag according to various arrangements.

FIG. 3C illustrates a perspective view of the placemat system 300 shown in FIG. 3A that is transformed into a carrying bag according to various arrangements.

Referring to FIGS. 3A and 3C, in some arrangements, each of the drawstrings 304a, 304b is a sterile or non-sterile cord or drawstring and is received in the drawstring casing 302 and is of a size to extend about the periphery of the placemat system 300. In some arrangements, the drawstrings 304a, 304b are slidably received in the drawstring casing 302 so that their movement within the drawstring casing 302 about the periphery of placemat system 300 is unrestricted. In some arrangements, to change the configuration of the placemat system 300 from a placemat to a carrying bag (e.g., for disposing, the top and bottom drawstrings 304a, 304b are pulled away from the drawstring casing 302 through their respective openings (e.g., 303a and 303b). The drawstrings 304a and 304b are pulled in a direction out of and away from the drawstring casing 302.

As the top and bottom drawstrings 304a, 304b are pulled out of their respective openings, the drawstring casing 302, the first material 102, the second material 104, and any other layer included in the placemat system 300 form gathers adjacent the periphery, of the placemat system 300 to permit the periphery thereof to reduce in size. The drawing together or contraction of the drawstring casing 302 causes the casing 302 to pucker or ruffle to form the gathers. The first material 102 and second material 104 (and any other layer of material, for example, an absorbent material) adjacent the drawstring casing 302 also pucker or contract together as the gathers are formed. in some arrangements, the drawstring casing 302 is located more towards the center of the placemat system 300, for example, such that the drawstring casing 302 forms a square shape within the rectangular shape of the placemat system 300.

In some arrangements, as the periphery of the placemat system 300 reduces in size and the gathers are formed, the edges of the placemat system 300 are drawn together to cause the placemat system 300 to form a carrying bag. When the placemat system 300 defines a carrying bag, the first material 102 forms an outer surface of the carrying bag and the second material 104 forms an interior surface of the carrying bag. in some arrangements, when formed as a carrying bag, procedural equipment, procedural waste, and other procedural materials (e.g., disposable materials), such as gel applicators, gel dispensers, protective bags, sanitizing wipes, and the like, can be carried within the carrying bag. In some arrangements, because of the pliable nature of the materials of the placemat system 300, it is a highly efficient carrier of materials, capable of defining its shape about the articles to be carried and cushioning the contents therein and having a large capacity or carrying volume. Also, due to the impermeability and sterility of the construction of the first material 102 and its facing opposite of the procedural surface of the second material 104, a containment bag for biohazard waste having a sterile or non-sterile outer surface is formed without the use of an external separate containment component having to be employed or the placemat and equipment having to be placed within.

In some arrangements, after the drawstrings 304a, 304b are pulled from the drawstring casing 302 such that the carrying bag is formed, a handle portion for the carrying bag is created by securing the extended drawstrings 304a, 304b together once they have been pulled out of their respective openings (e.g., openings 303a, 303b). In some arrangements, the extended drawstrings 304a, 304b are secured together by tying them together or by other suitable fastening methods.

In some arrangements, by forming the placemat system 300 as a carrying bag, the placemat system 300 can be easily transported from the procedural area while carrying equipment, waste, or other articles. In some arrangements, because the carrying bag has a layer of absorbent material (e.g., the second material 104) at the interior surface, the articles carried therein are cushioned and protected from possible damage during transport as a result of the density and padding properties of the second material 104, in some arrangements, the pliable characteristics of the carrying bag permit it to take the configuration of the articles being transported as well.

Figure 4:
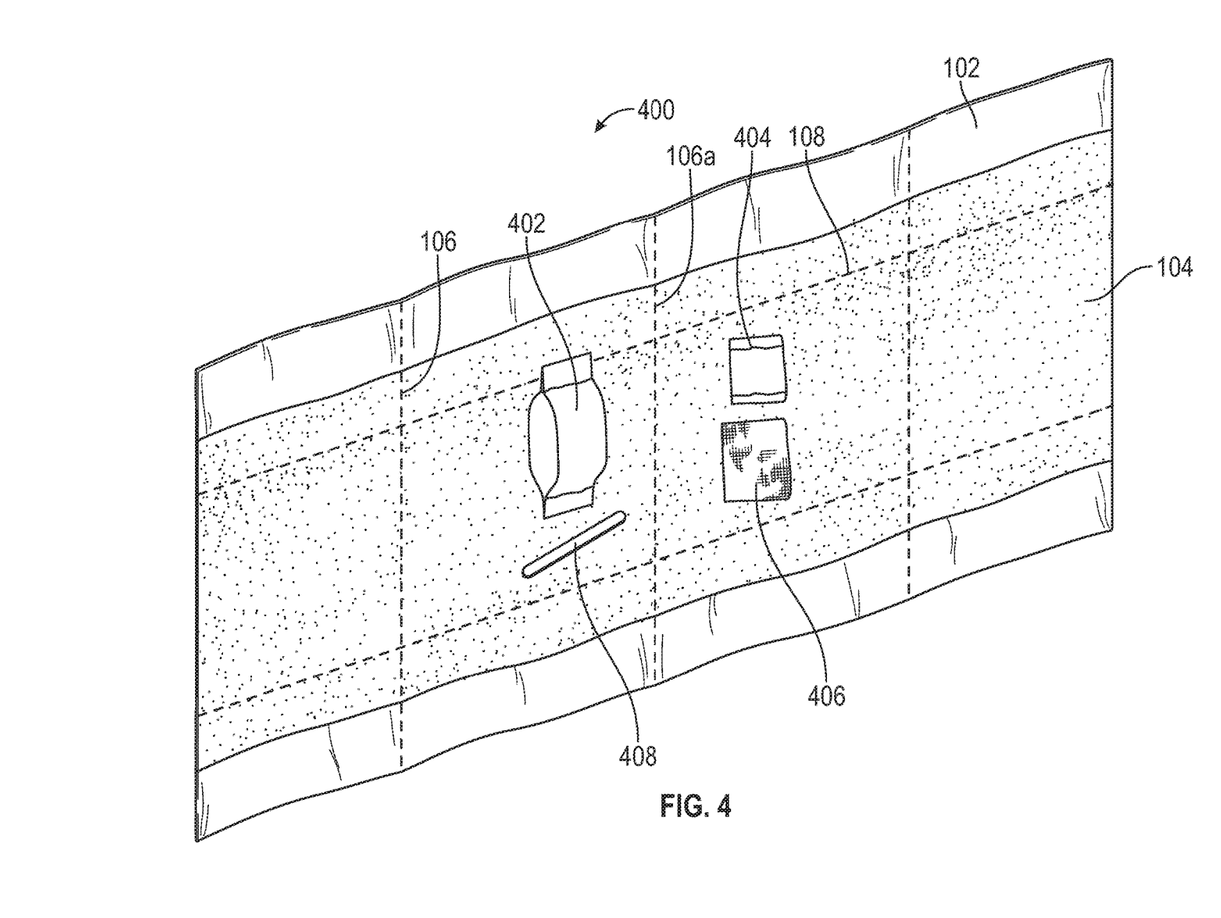
FIG. 4 illustrates a top view of a placemat system including one or more instruments therein according to various arrangements.

FIG. 4 illustrates a top view of a placemat system 400 having one or more instruments 402, 404, 406, 408 placed thereon according to various arrangements.

Referring to FIG. 4, the placemat system 400 may include at least the placemat system 100, for example, having a sheet of the first material 102, a sheet of the second material 104, the folding guides 106, 106a, and 108, and the like. In some arrangements, the instruments 402, 404, 406, 408 include any object for use in connection with a medical procedure (e.g., an ultrasound scan operation). The instruments 402, 404, 406, and 408 may be objects such as, but not limited to, gel (e.g., ultrasound gel), pincers, sanitizing wipes, gauze, gel applicators, and so on. In some arrangements, the instruments 402, 404, 406, 408 are placed within the placemat system 400 after use in a medical procedure, and both the instruments 402, 404, 406, 408 and the placemat system 400 are disposed of. For example, the placemat system 400 is folded with the instruments 402, 404, 406, 408 therein and disposed of, or the placemat system 400 is cinched (e.g., using the drawstrings 304a, 304b) with the instruments 402, 404, 406, 408 therein and then disposed of.

Figure 5:
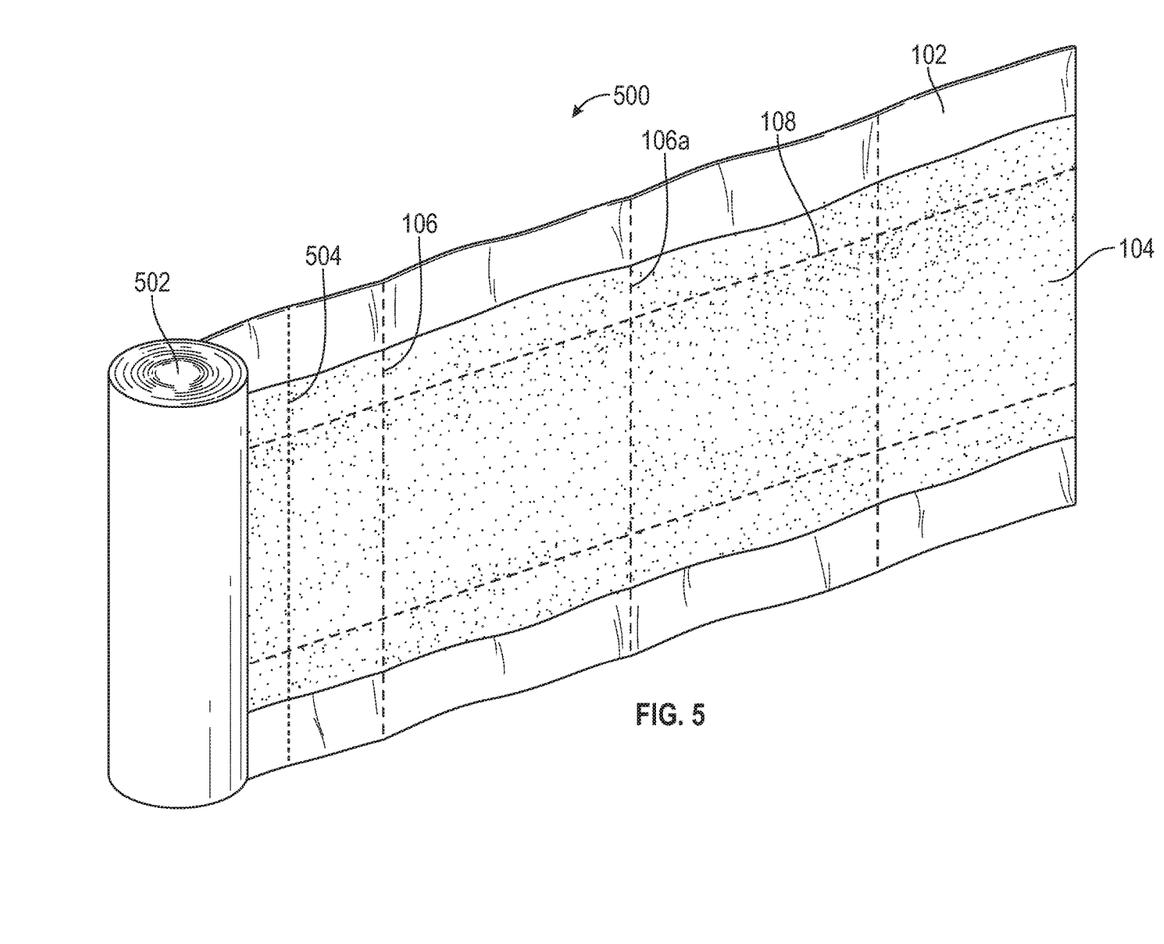
FIG. 5 illustrates a top view of a roll of placemat systems according to various arrangements.

FIG. 5 illustrates a top view of a roll 502 of placemat systems 500 according to various arrangements.

Referring to FIG. 5, each of the placemat systems 500 may include at least the placemat system 100, for example, having a sheet of the first material 102, a sheet of the second material 104, the folding guides 106, 106a, and 108, and the like. In some arrangements, the plurality of placemat systems 500 is stored in the roll 502. In particular arrangements, any two adjacent ones of the placemat systems 500 are separated by a perforated section 504 such that a user can tear away individual ones of the placemat systems 500 for use. Accordingly, in some arrangements, placemat systems can be manufactured easily by making an extended sheet of placemat systems 500 that is separated by perforated sections 504 and then stored as the roll 502 for easy transportation of the plurality of placemat systems 500.

Figure 6:
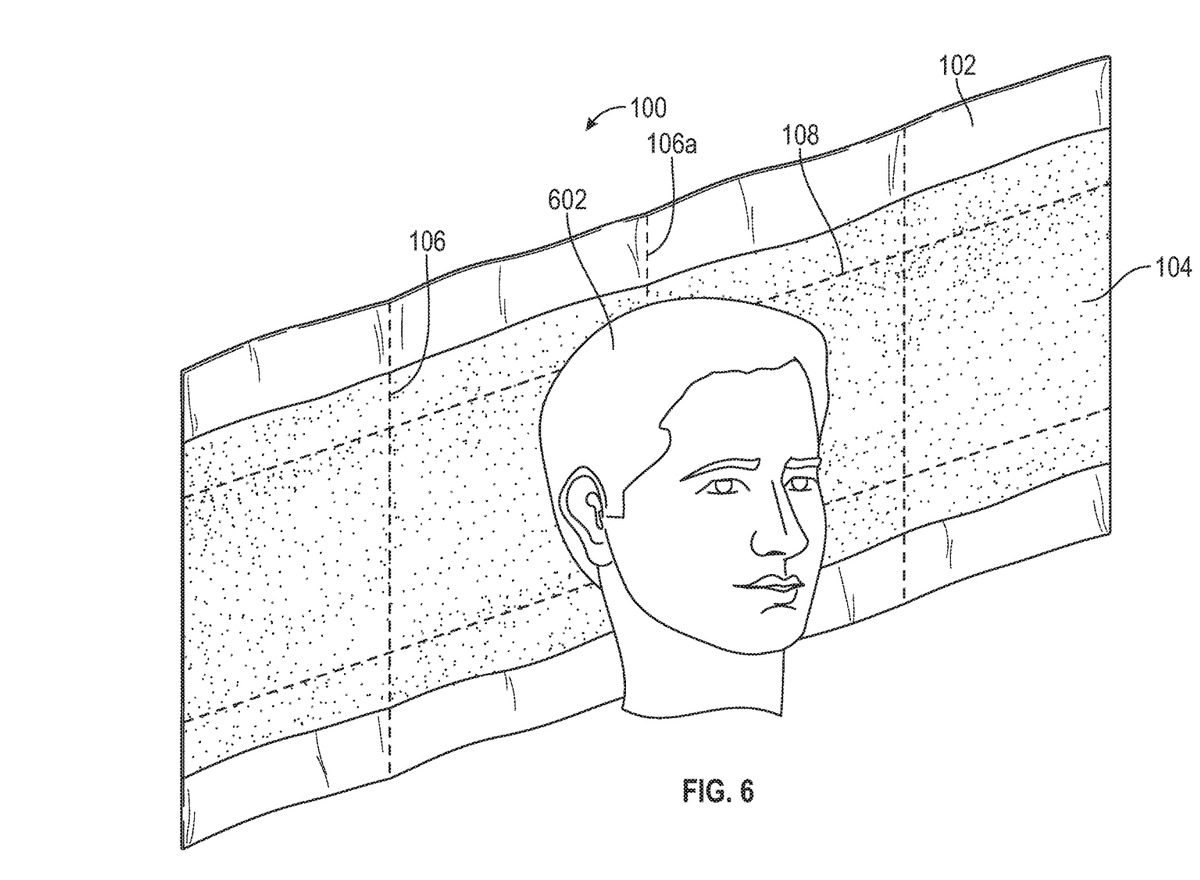
FIG. 6 illustrates a top view of a placemat system and a human head placed thereon according to various arrangements.

FIG. 6 illustrates a top view of the placemat system 100 and a subject's head 602 (e.g., a human head) placed thereon according to various arrangements.

Referring to FIGS. 1 and 6, in some arrangements, the subject's head 602 is centered on the placemat system 100 so that there are substantially equal lengths of the placemat system 100 extending horizontally from both sides of the subject's head 602 (e.g., so that any liquid or materials from the medical procedure are received by the placemat system 100 and not by the surface underneath the placemat system 100). To this end, the placemat system 100 serves as a subject placement marker for indicating the appropriate location to position the head 602. For example, by placing the placemat system 100, a healthcare administrator can utilize the central vertical folding guide 106a as a marker for adequately positioning the subject's head 602 (or any other body part or piece of medical equipment).

Figure 7A:
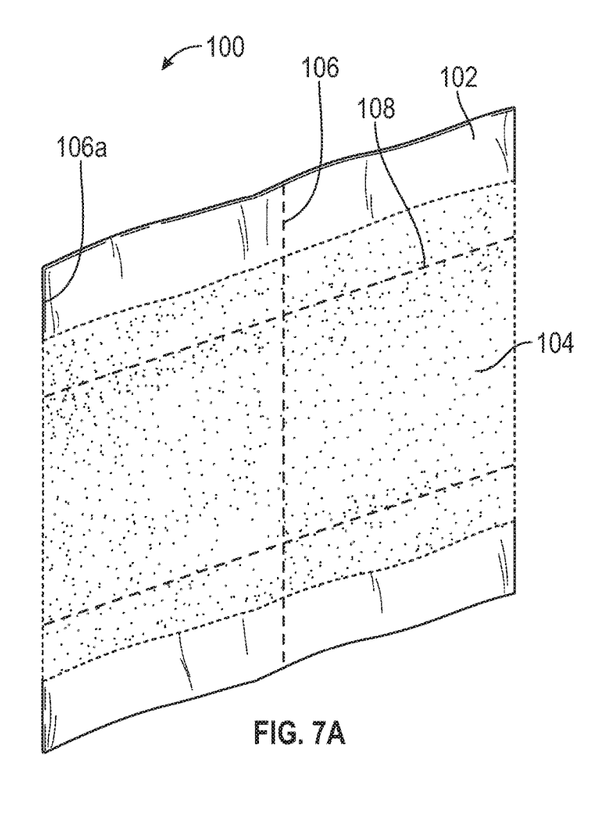
FIG. 7A, FIG. 7B, and FIG. 7C illustrate top views of a placemat system at different folded stages according to various arrangements.
Figures 7B, 7C:
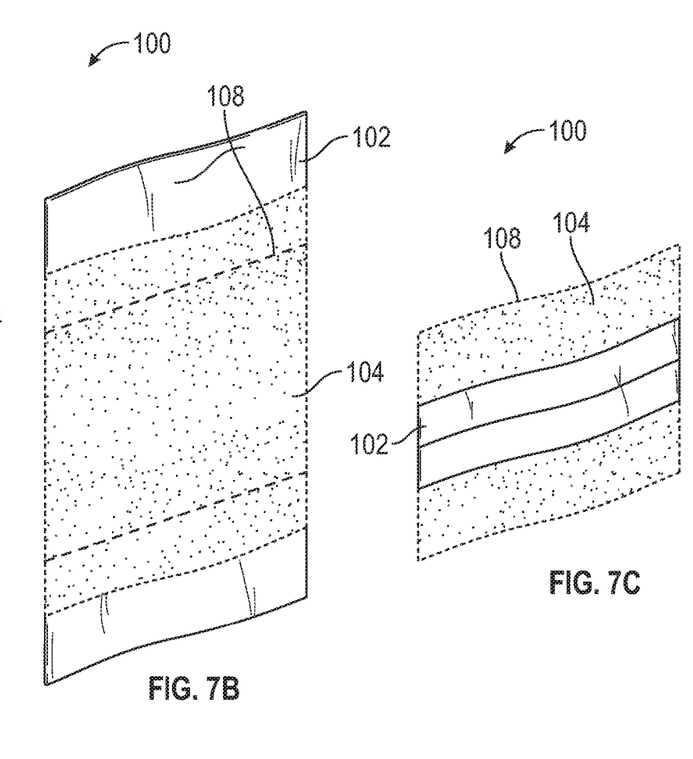

FIG. 7A, FIG. 7B, and FIG. 7C illustrate top views of the placemat system 100 at different folded stages according to various arrangements.

Referring to FIGS. 1 and 7A, in some arrangements, the placemat system 100 is first folded along the central vertical folding guide 106a such that the placemat system 100 is folded in half. Referring to FIGS. 1 and 7B, in some arrangements, the placemat system 100 is then folded along another vertical folding guide 106 such that all the vertical folding guides 106 have been folded upon. Referring to FIGS. 1 and 7C, in some arrangements, the placemat system 100 is then folded along each of the horizontal folding guides 108 so that the top and bottom portions of the folded placemat system shown in FIG. 7B (e.g., the portion above the top horizontal folding guide 108 and the portion below the bottom horizontal folding guide 108, respectively) are folded on top of each other.

While the figures illustrate various features of the placemat systems 100, 200, 300, 350, 400, and 500, one of ordinary skill in the art can appreciate that the features described with reference to the different figures can be combined in any suitable combination or permutation as desired.

Figure 8A:
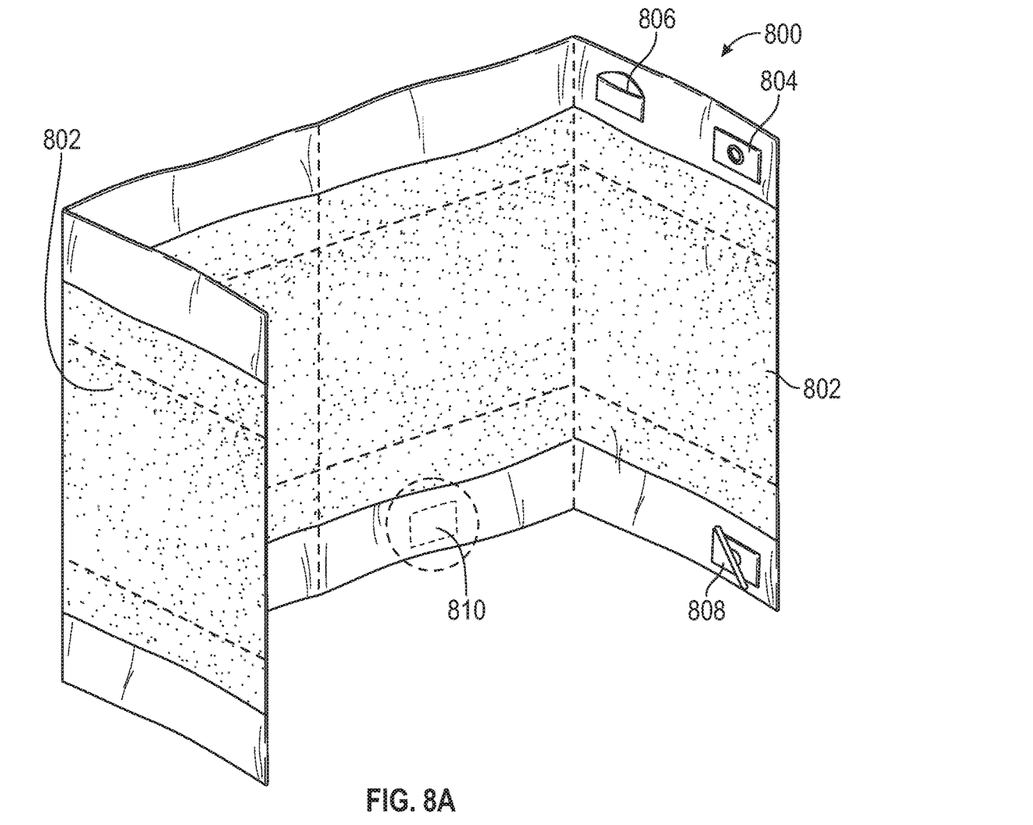
FIG. 8A illustrates a perspective view of a placemat system according to various arrangements.

FIG. 8A illustrates a perspective view of a placemat system 800 according to various arrangements.

Referring to FIG. 8A, in some arrangements, the placemat system 800 is similar to the placemat system 100, and so the description above is applicable to the placemat system 800. In some arrangements, the placemat system 800 includes barrier wings 802, a first anchor 804, a second anchor 806, a third anchor 808, and a fourth anchor 810.

In some arrangements, the barrier wings 802 are foldable so as to either lay flat on top of a work surface or extend upwards (e.g., perpendicularly) from the work surface. Accordingly, the barrier wings 802 are made from any suitable rigid material, such as, but not limited to, cardboard, plastic, and the like. In some arrangements, the barrier wings 802 fold along a vertical folding guide (described above). In some arrangements, by folding and remaining upwards, the barrier wings 802 prevent any fluid (e.g., fluid from a subject or fluid used in connection with a medical procedure) from leaking beyond the placemat system 800 and onto the work surface, thereby improving infection control and hygiene with respect to the different patients that are placed on the work surface. In some arrangements, the top and/or bottom of the placemat system 800 include barrier wings 802 such that three or all four edges of the placemat system 800 are walled off by the barrier wings 802 to prevent any leakage of fluid from within the placemat system 802 and onto the work space.

In some arrangements, the placemat system 800 include the first anchor 804 that has a slot therein for receiving a piece of medical equipment. In particular arrangements, the medical equipment can be a piece of equipment used in conjunction with a medical procedure for which the placemat system 800 is also used for. For example, the placemat system 800 can be used in connection with an automated TCD and the piece of medical equipment can include a camera that is slotted into the first anchor 804 so that the camera can monitor the patient or can take a picture of the patient for optically registering the patient with respect to the automated TCD.

In some arrangements, the second anchor 806 includes a pocket for retaining one or more medical instruments. For example, the second anchor 806 can retain one or more reflective fiducial stickers for placing at anatomically significant locations on a patient's head (e.g., at the corner of the eye and at the tragus of the patient) so that the patient can be optically registered by a camera (as discussed above) for use in connection with an automated robotic TCD system. In some arrangements, the third anchor 808 includes a magnet. Accordingly, various metallic medical instruments can be retained by the third anchor 808 during, before, or after a medical procedure. Such metallic medical instruments include, but are not limited to, pincers, a scalpel, a gel applicator, and so on. In some arrangements, the first anchor 802, the second anchor 804, and the third anchor 806 are located at any suitable and convenient location of the placemat system 800, such as, but not limited to, the corners, any portion of an edge, at the central portion, and so on.

Figure 8B:
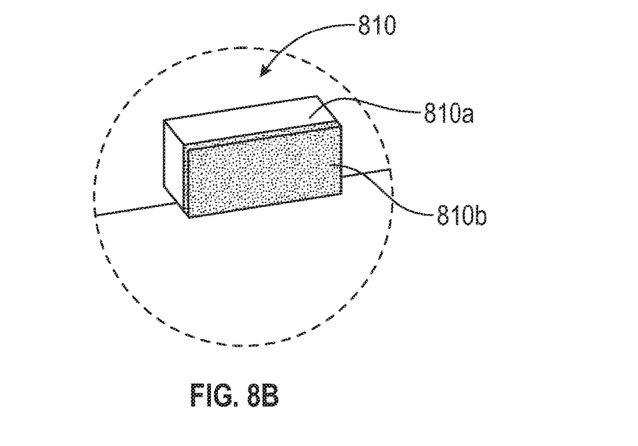
FIG. 8B illustrates an enlarged perspective view of the anchor shown in FIG. 8A according to various arrangements.

FIG. 8B illustrates an enlarged perspective view of the fourth anchor 810 shown in FIG. 8A according to various arrangements.

Referring to FIGS. 8A-8B, the placemat system 800 includes the fourth anchor 810 located at the back surface thereof, or the surface that is configured to contact the work surface. The fourth anchor 810 includes an anchor weight 810a and an adhesive layer 810b on the anchor weight 810. In some arrangements, the anchor weight 810a is a weighted block configured to anchor the placemat system 800 to the work surface. In some arrangements, the adhesive layer 810b is configured to affix the placemat system 800 to the work surface to provide a stronger anchor by the fourth anchor 810. As such, the fourth anchor 810 enables the placemat system 800 to remain stable with respect to a work surface and a patient placed on the placemat system 800. In some arrangements, any suitable number of fourth anchors 810 are provided at the back surface of the placemat system 800 for suitably affixing and stabilizing the placemat system 800, such as, but not limited to, two, three, four, or more. In some arrangements, the one or more fourth anchors 810 are located at any suitable location of the placemat system 800 for suitable stabilization, such as, but not limited to, the top edge, the bottom edge, the side edges, the corners, and so on.

The above used terms, including "held fast," "mount," "attached," "coupled," "affixed," "connected," "secured," and the like are used interchangeably. In addition, while certain arrangements have been described to include a first element as being "coupled" (or "attached," "connected," "fastened," etc.) to a second element, the first element may be directly coupled to the second element or may be indirectly coupled to the second element via a third element.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

What is claimed is:

1. A disposable placemat system comprising:
    a sheet of a first material having a front surface and a back surface opposite to the front surface;
    a sheet of a second material attached to the sheet of the first material at the front surface and exposing an uncovered portion of the sheet of the first material; and
    one or more anchors attached to the uncovered portion of the sheet of the first material, wherein
        the first material is liquid impermeable and different from the second material, and
        the second material is absorbent.

2. The placemat system of claim 1, wherein the one or more anchors includes a plurality of anchors.

3. The placemat system of claim 2, wherein the plurality of anchors includes four anchors.

4. The placemat system of claim 1, wherein the one or more anchors are attached to the front surface of the sheet of the first material.

5. The placemat system of claim 1, wherein the one or more anchors include an adhesive.

6. The placemat system of claim 1, wherein the one or more anchors are attached to the back surface of the sheet of the first material.

7. The placemat system of claim 1, wherein the one or more anchors include a weighted block.

8. The placemat system of claim 1, further comprising a plurality of placemat systems and a roll configured to store the plurality of placemat systems.

9. The placemat system of claim 8, wherein each adjacent pair of placemat systems of the plurality of placemat systems is separated by a perforated section.

10. A method of manufacturing a disposable placemat system comprising:
    providing a sheet of a first material having a front surface and a back surface opposite to the front surface;

providing a sheet of a second material attached to the sheet of the first material at the front surface and exposing an uncovered portion of the sheet of the first material; and providing one or more anchors attached to the uncovered portion of the sheet of the first material, wherein the first material is liquid impermeable and different from the second material, and the second material is absorbent.

11. The placemat system of claim 4, wherein the one or more anchors are adjacent to the sheet of the second material.

12. The placemat system of claim 1, wherein the sheet of the second material is uncovered.

13. The placemat system of claim 1, wherein the sheet of the second material is a continuous sheet.

14. The placemat system of claim 13, wherein the sheet of the second material is continuous from a first edge of the sheet of the first material to a second edge of the sheet of the first material opposite the first edge.

15. The placemat system of claim 1, wherein the one or more anchors include a string.

16. The placemat system of claim 1, wherein the one or more anchors include an elastic band.

17. The placemat system of claim 1, wherein the uncovered portion of the sheet of the first material defines an isolated continuous strip of the sheet of the first material.

18. The placemat system of claim 17, wherein the isolated continuous strip of the sheet of the first material is located along an edge of the placemat system.

19. The placemat system of claim 1, wherein the uncovered portion of the sheet of the first material defines a plurality of disconnected strips of the sheet of the first material.

20. The placemat system of claim 18, wherein the plurality of disconnected strips of the sheet of the first material are separated by the sheet of the second material.

* * * * *